United States Patent
Baloche et al.

(10) Patent No.: US 8,822,701 B2
(45) Date of Patent: *Sep. 2, 2014

(54) METHOD FOR PREPARING AND USING AMINOETHYL IMIDAZOLIDINONE AND THE THIOCARBONYL THEREOF

(71) Applicant: Arkema France, Colombes (FR)

(72) Inventors: Alain Baloche, Annay (FR); Jean-Paul Gamet, Savy-Berlette (FR); Jean-Philippe Gillet, Brignais (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/944,355

(22) Filed: Jul. 17, 2013

(65) Prior Publication Data

US 2013/0303784 A1 Nov. 14, 2013

Related U.S. Application Data

(63) Continuation of application No. 13/521,486, filed as application No. PCT/FR2011/050029 on Jan. 7, 2011, now Pat. No. 8,513,435.

(30) Foreign Application Priority Data

Jan. 11, 2010 (FR) .................................. 10 50127

(51) Int. Cl.
  *C07D 233/32* (2006.01)
  *C07D 233/36* (2006.01)
  *C07D 233/42* (2006.01)

(52) U.S. Cl.
  CPC ............ *C07D 233/36* (2013.01); *C07D 233/42* (2013.01)

USPC .................................. 548/324.5; 548/325.1

(58) Field of Classification Search
None
See application file for complete search history.

(56) References Cited

U.S. PATENT DOCUMENTS

| | | | |
|---|---|---|---|
| 2,613,212 | A | 10/1952 | Hurwitz et al. |
| 4,104,220 | A | 8/1978 | Sims |
| 4,491,527 | A | 1/1985 | Lange et al. |
| 5,746,946 | A | 5/1998 | He et al. |
| 6,013,200 | A | 1/2000 | Prince |
| 2009/0270372 | A1 | 10/2009 | Poitout et al. |
| 2010/0273965 | A1 | 10/2010 | Hidalgo et al. |
| 2011/0003872 | A1 | 1/2011 | Tournilhac et al. |
| 2012/0276274 | A1 | 11/2012 | Froes et al. |

FOREIGN PATENT DOCUMENTS

| | | |
|---|---|---|
| DE | 199 57 348 A1 | 5/2000 |
| FR | 2 924 715 A1 | 6/2009 |
| FR | 2 925 504 A1 | 6/2009 |
| WO | WO 97/49676 | 12/1997 |
| WO | WO 2009/114566 A1 | 9/2009 |
| WO | WO 2009/138438 A1 | 11/2009 |
| WO | WO 2009/142569 A1 | 11/2009 |

OTHER PUBLICATIONS

International Search Report for International Appl. No. PCT/FR2011/050029, Dated Apr. 28, 2011.

*Primary Examiner* — Michael Barker
*Assistant Examiner* — Po-Chih Chen
(74) *Attorney, Agent, or Firm* — RatnerPrestia

(57) ABSTRACT

The present invention relates to a method for preparing 1-(2-aminoethyl)imidazolidin-2-one or the thiocarbonyl thereof, and also to the product that can be obtained according to this method, and which has a purity of at least 98%, and to the uses thereof.

18 Claims, No Drawings

METHOD FOR PREPARING AND USING AMINOETHYL IMIDAZOLIDINONE AND THE THIOCARBONYL THEREOF

CROSS REFERENCE TO RELATED APPLICATIONS

This application is a Continuation application of U.S. application Ser. No. 13/521,486, filed Jul. 11, 2012, which is a U.S. National Phase under 35 U.S.C. §371 of PCT International Application No. PCT/FR2011/050029, filed 7 Jan. 2011, and published 14 Jul. 2011 in French as WO 2011/083281 A1, which claims priority from French Application FR 10 50127, filed 11 Jan. 2010, the contents of each of which are incorporated by reference in their entirety for all purposes.

FIELD OF THE INVENTION

The present invention relates to a process for preparing 1-(2-aminoethyl)imidazolidin-2-one or the thiocarbonyl thereof, and also to the product that can be obtained according to this process, and which has a purity of at least 98%, and to the uses thereof.

BACKGROUND 1-(2-Aminoethyl)imidazolidin-2-one (hereinafter, UDETA) is a compound, corresponding to the following formula:

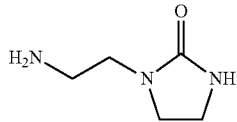

which has the advantage of having not only a reactive primary amine function that makes it possible to envision its condensation on numerous carbonyl derivatives, but also free electron doublets capable of producing hydrogen bonds between the molecules onto which it is grafted or between these molecules and other molecules bearing associative groups. UDETA is thus used, in particular, for the synthesis of supramolecular materials (FR2924715). The applicant has also proposed using UDETA as a salifying agent, for producing a styrene/maleic anhydride copolymer-based additive intended for coating or sizing paper (FR2925504). UDETA is also involved in the production of pharmaceutical compounds (as described, in particular, in WO 2009/142569, US 2009/270372, WO 2009/114566 and WO 2009/138438), of phytosanitary products, in particular pesticides, or of additives for paints or lubricants (U.S. Pat. No. 5,746,946).

U.S. Pat. No. 2,613,212 is one of the first to describe the synthesis of UDETA. In said document, it is indicated that UDETA can be obtained by reacting at least one mole of diethylenetriamine (or DETA) with one mole of urea, and preferably an equimolar amount of these reactants, at a temperature of from 100 to 300° C. In the examples of said document, the molar ratio of the DETA to the urea is abut 1.2. The mixture is heated to 210 or 250° C. The product obtained is then distilled under reduced pressure at 155-163° C. An application of this process is illustrated in example 1 of U.S. Pat. No. 5,746,946 probably, using a DETA:urea molar ratio of 1:1 and using reaction and distillation temperatures of at most 150° C. It is indicated in said document that the product obtained has a purity of 95%. However, the inventors have demonstrated, by reproducing this example, that it results in a product containing approximately 63% of UDETA only. The difference with the value indicated in U.S. Pat. No. 5,746,946 comes from the fact that, in said patent, the purity is defined in terms of an alkalinity measurement, which is not sufficient to exclude the presence of impurities containing amine functions and themselves generating a certain alkalinity.

In an analogous manner, U.S. Pat. No. 4,491,527 (example 2) has described a process for synthesizing UDETA using a mixture of DETA and urea in a DETA:urea molar ratio of 2:1, which is brought to 203° C. The product obtained is then distilled under reduced pressure, at a temperature of 165-175° C.

Comparative example 1 of application DE 199 57 348 also discloses a process for synthesizing a product containing "predominantly" UDETA, from a mixture of equimolar amounts of DETA and urea, brought to 155° C. Another process of this type is illustrated by example C of application WO 97/49676. In this example, the DETA/urea molar ratio is approximately 1 and the mixture is heated to 210° C. before being distilled under reduced pressure at more than 175° C.

The UDETA obtained according to these processes contains, like the commercial UDETA used in U.S. Pat. No. 4,104,220, a significant amount of impurities. The commercially available qualities of standard UDETA thus generally have a UDETA titer of approximately 85%.

For certain applications, in particular for the synthesis of supramolecular compounds, it would, however, be desirable to be able to have available a UDETA quality having a purity of at least 90%, for example of at least 95%. In particular, if the UDETA must be used as a synthon in pharmaceutical chemistry, a purity of at least 98%, or even of at least 99%, is even sought. Moreover, it is desirable to have available a UDETA quality containing less than 5%, or even less than 3%, by weight of TETU, less than 1% by weight of DETA, less than 5% by weight of DETA-urea-DETA and/or less than 1% by weight of organic solvent.

Among the major impurities present in the UDETA obtained according to the prior art processes, mention may be made of the residual DETA, and also TETU or N,N'-bis[2-(2-oxo-1-imidazolindinyl)ethyl] and the condensation product DETA-urea-UDETA. The presence of DETA is in particular problematic in the field of the synthesis of supramolecular compounds, insofar as it has several reactive groups capable of forming undesirable bonds with the other synthons used in the synthesis of these compounds.

The means used up until now to reduce the amount of these impurities comprise in particular the purification of the UDETA by extraction in a solvent. The company King Industries thus proposes a UDETA grade which is purer than the standard grades, but which contains large amounts of solvent (about 9%) which may be prejudicial in certain applications. Another means of UDETA purification consists of distillation under vacuum or reduced pressure, which is usually carried out at a temperature greater than 150° C., and generally of at least 160° C., as previously indicated. However, the inventors have demonstrated that these distillation conditions lead to a retrogradation of the UDETA to give DETA and TETU. Specifically, the conventional vacuum distillation technique is reflected by an increase in the TETU content at the bottom of the column and by the accumulation of a UDETA/DETA mixture at the top. This retrogradation affects the purity of the UDETA, and also the reaction yield.

Supported by this observation, the inventors have subsequently demonstrated that the purity of the UDETA is also affected by the DETA:urea molar ratio, which influences the TETU content. Specifically, the lower this ratio, the larger the amount of TETU formed. Following many experiments, they have thus demonstrated that adjusting these two parameters (distillation conditions and DETA:urea ratio) in given ranges makes it possible to obtain a product that can reach a very high UDETA purity, according to a process that is simple and economical to implement, in particular in terms of energy consumption and owing to the absence of any recourse to a solvent purification step. They have also demonstrated that this process can be transposed to the preparation of the thiocarbonyl of UDETA.

SUMMARY OF THE INVENTION

The subject of the present invention is thus a process for preparing a compound of formula (I):

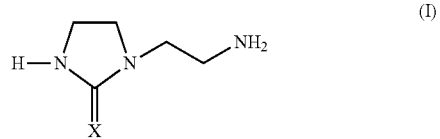

where X is oxygen or sulfur,
comprising the successive steps consisting in:
1) reacting diethylenetriamine (DETA) with a urea compound chosen from urea and thiourea, in a DETA/urea compound molar ratio of between 1.2 and 1.9 or between more than 1.9 and 3, at a temperature of at most 300° C.;
2) cooling the reaction medium;
3) removing the residual DETA by distillation under reduced pressure at a temperature, at the bottom of the column, of at most 150° C.

This process makes it possible to obtain a compound which has a high purity, of at least 90%, optionally of at least 95%, or even of at least 98% or even of at least 99%, by adjusting the parameters of this process. The UDETA obtained usually contains less than 5%, or even less than 3%, by weight of TETU, less than 1% by weight of DETA, less than 5% by weight of DETA-urea-DETA and/or less than 1% by weight of organic solvent. These values can be measured in a manner conventional for those skilled in the art, by gas chromatography (GC) or high performance liquid chromatography (HPLC).

In addition, the recourse to a low distillation temperature has advantages in terms of energy saving, and also limits the degradation of the product and therefore in particular its coloration.

DETAILED DESCRIPTION OF THE INVENTION

In one embodiment of the invention, the residual DETA can, in addition, be recycled into the process, given its quality, and the ammonia given off by the reaction can itself be recovered, for example so as to be conveyed to a unit for the synthesis of fatty amines via the nitrile route, after distillation of the aqueous ammoniacal liquors. The economy of the process is thus further improved.

The steps of the process according to the invention and the reactants used for the implementation thereof will now be described in greater detail.

By way of preamble, it will be noted that the expression "between" should be interpreted, in the present description, as including the limits cited.

In the first step of the process according to the invention, a urea compound (urea or thiourea) is reacted with DETA, in a DETA/urea compound molar ratio of between 1.2 and 1.9 or between more than 1.9 and 3.0, preferably between 1.3 and 1.7 and more preferentially between 1.3 and 1.6. In the interests of simplicity, the urea compound can be introduced in the form of an aqueous solution, for example at 40% in water. It is however possible, as a variant, to use the urea in solid form.

According to one advantageous embodiment of the invention, the urea compound is introduced into the reaction medium sequentially, preferably in fractions of from 10 to 40% by weight relative to the total weight of the urea compound processed. In this case, the period of time between the introduction of two successive fractions (advantageously of decreasing weight) may be between 30 min and 1 h 30, for example may be approximately 1 h. This fractionwise introduction makes it possible to limit the concentration of free urea that can result in the formation of TETU, to limit the thermal decomposition of the urea and to slowly remove the diluting water, without entraining too much DETA. It thus contributes to increasing the purity of the UDETA obtained.

The urea compound can be mixed with the DETA before the reaction medium is heated. However, the urea compound is preferably introduced into the heated reaction medium containing the DETA.

Said reaction medium is heated at a temperature of less than 300° C., for example between 100 and 250° C., or even between 100 and 200° C. The temperature of the reaction medium is advantageously gradually increased during the reaction, between the temperature at which the urea compound is introduced and the final temperature of the reaction, so as to be preferably brought from 110-140° C. to 150-190° C., for example in steps of 10 to 20° C. The reaction medium can, in this case, be maintained at the temperature of each step for a period of time ranging from 30 min to 6 h. It is thus possible to control the kinetics of the main reaction and of the parasitic reactions and, subsequently, to limit the formation of TETU and to convert a maximum of the DETA-urea-DETA, formed as a by-product of the reaction, into UDETA.

The reaction medium is then cooled, for a period of time ranging, for example, from 30 minutes to 3 hours, and it is then subjected to a distillation step at a temperature, at the bottom of the column, of at most 150° C., for example between 100 and 140° C., preferably between 120 and 130° C. The distillation is carried out under reduced pressure, i.e. under a pressure of from 30 to 1 mbar, preferably from 10 to 1.5 mbar. It is, for example, carried out over a maximum period of 5 hours.

It is advantageously a molecular distillation.

Molecular distillation is a continuous evaporation under a strong vacuum of a thin film of product that is moving between a hot surface (the evaporator), the surface area of which can range, for example, from 0.01 to 50 m$^2$, and a cold surface (the condenser).

The molecular distillation can be carried out in a wiped-film still. Wiped-film stills comprise a distillation chamber which has a rotating wiping device, such as a PTFE/silica roll wiper, which makes it possible (in particular under the effect of centrifugal force) to continuously spread, over the evaporator, the product to be distilled. These stills generally operate under a pressure of from 1 to 100 mbar. The product vapors are evacuated via an orifice located in the top part of the still, before being condensed or conveyed to a rectification column. In a short-path still, the vapors are condensed by the condenser placed at the center of the distillation chamber and the vacuum created can range up to 0.001 mbar.

In any event, the residue and the distillate are recovered by gravitational flow.

Molecular stills are in particular commercially available from the companies VTA GmbH, UIC GmbH, FT Technologies and Pope Scientific, Inc.

According to the invention, it is preferred to use a short-path/wiped-film distillation process. This process makes it possible to obtain the UDETA with a purity of greater than 95%.

In order to further increase the purity of the UDETA, the molecular distillation process can advantageously comprise the following two successive steps:

1—a first distillation at a temperature of from 110° C. to 120° C., under a pressure of from 1 to 2 mbar, for example from 1.5 to 2 mbar, 2—a second distillation at a temperature between more than 120° C. and 135° C., under a pressure of from 0.005 to 0.02 mbar, for example from 0.01 to 0.015 mbar.

This variant makes it possible to obtain a particularly pure product, having a purity of greater than 99%, with a yield (rate of recovery of UDETA or of the thiocarbonyl thereof) of from 85 to 90% without recycling of the bottom fraction.

After this distillation step, the process according to the invention generally comprises a step of readjusting the pressure to atmospheric pressure and of cooling, before recovering the compound produced.

The process according to the invention thus makes it possible to obtain a compound which has a high purity, optionally of at least 98% or even of at least 99%, by adjusting the parameters of this process and in particular the DETA/urea compound molar ratio and the distillation conditions, as emerges from the examples hereinafter. To the knowledge of the inventors, UDETA and the thiocarbonyl derivative thereof have never yet been produced with this purity on an industrial scale.

The subject of the present invention is therefore also the product that can be obtained according to the process described above, wherein it contains at least 98% by weight, preferably at least 99% by weight, of compound of formula (I).

The product obtained according to the invention can be used as a synthesis synthon or reactant in many applications, and in particular for the production of supramolecular materials, of pharmaceutical compounds, of phytosanitary products, or of additives for paints, paper or lubricants.

The subject of the invention is therefore also these uses.

The invention will be understood more clearly in the light of the following examples, given for the purposes of illustration only, and the objective of which is not to limit the scope of the invention, which is defined by the appended claims.

EXAMPLES

Example 1

Preparation of UDETA from DETA and Urea
(R=1.5)

693 kg (6728 M) of DETA were introduced into a 1 m³ stirred reactor which has a double jacket, a device for introducing liquid, a nitrogen inerting system, a container and a scrubbing column for recovering the ammonia gas and the aqueous ammoniacal liquors. The reaction medium was brought to 130° C. while at the same time performing nitrogen sparging so as to deoxygenate the DETA. When the temperature was reached, the introduction of an aqueous solution of urea at 40%, on the basis of 671.4 kg (4476 M), was begun. The DETA:urea molar ratio was therefore 1.5:1.

The urea was introduced fractionwise over the course of 4 h.

The release of ammonia, which appeared at soon as the running-in began, was scrubbed on the scrubbing column and the aqueous ammoniacal liquors were collected in the container. The reaction mixture was then kept at 130° C. for 1 h 30 in order to finish off the removal of the water.

The reaction medium was then gradually heated by bringing it: to 140° C. for 45 min, then to 150° C. for 45 min, then to 160° C. for 5 h. It was cooled to 125° C. at the end of the reaction, and then the excess DETA was removed under reduced pressure of from 10 to 1.5 mbar and with mild nitrogen sparging, for a maximum of 5 h. The product obtained after returning the equipment to atmospheric pressure, cooling to 60° C. and withdrawal from the reactor had a UDETA titer of 95-96% and contained 1-2.5% of TETU.

Example 2

Preparation of UDETA from DETA and Urea
(R=1.25)

The same process as that described in example 1 was carried out, except that the DETA/urea molar ratio was 1.25:1. The final product had a UDETA titer of 93% and contained 0.5% of residual DETA and 2.7% of TETU.

Example 3

Preparation of UDETA from DETA and Urea (R=2)

The same process as that described in example 1 was carried out, except that the DETA/urea molar ratio was 2:1 and the product obtained was subjected to stripping under reduced pressure at 120° C. instead of 125° C. The final product had a UDETA titer of 95% and contained 0.2% of DETA, 0.4% of TETU and 4.4% of other impurities.

Example 4

Preparation of the Thiocarbonyl of UDETA from
DETA and Thiourea (R=1.5)

154.5 g (1.5 M) of DETA were charged to a 500 cm³ reactor fitted with a mechanical stirrer, a heating device, a Dean-Stark condenser, a dropping funnel specific for the introduction of a solid, a nitrogen inerting system and a series of wash bottles for trapping the ammonia. Said DETA was brought to 130° C. under nitrogen sweeping. 76 g (1 M) of solid thiourea were then introduced fractionwise over the course of 1 h 30, such that the DETA:thiourea molar ratio was 1.5:1.

Ammonia was given off over the course of the running-in. At the end of the running-in, the temperature of the reaction medium was brought from 130 to 160° C., in steps, over the course of 6 h. After having disconnected the wash bottles and installed a vacuum pump, the excess DETA was removed by distilling it at 125° C. under 3 mbar.

143 g of a reaction crude with a waxy appearance, having a 1-(2-aminoethyl)-2-imidazolidinethione purity of 90%, were obtained.

Example 5

Molecular Distillation of UDETA

Crude UDETA, at a titer of 92% and containing 1% of DETA, was fed, at a flow rate of 681 g/h, onto short-path/ wiped film distillation equipment (of the 4 dm² VKL 70 type from the company VTA), stabilized at a pressure of 1.9 mbar and at a double-jacket temperature of 120° C. After distillation for approximately 2 h, a residue of 1379 g having a UDETA titer of 93% and containing 0.2% of residual DETA, and a distillate of 27.5 g containing 60% of DETA, were obtained.

The residue was reintroduced into the distillation apparatus at a flow rate of 568 g/h, after stabilization of the double jacket at 125° C. and pressure at 0.012 mbar. A second distillation was then carried out for 38 min under these conditions, so as to obtain, firstly, a colorless distillate of 314 g having a UDETA titer of 99.8% and, secondly, a residue of 45 g having a UDETA titer of 39% and containing all the heavy impurities.

Owing to its very high purity, this distillate can in particular be used in the synthesis of pharmaceutical products.

Comparative Example 1

Preparation of UDETA from DETA and Urea (R=1.05)

42 kg (407.7 M) of DETA were introduced into a 60 l stirred reactor fitted with a double jacket, a device for introducing liquid, a nitrogen inerting system, a container and a scrubbing column for recovering the ammonia. The reaction medium was brought to 120° C. while at the same time carrying out nitrogen sparging (0.2 l/s) so as to deoxygenate the DETA. When the temperature was reached, the introduction of an aqueous solution of urea at 40%, on the basis of 58.4 kg (389 M), was begun. The DETA:urea molar ratio was therefore 1.05:1.

The urea was introduced fractionwise over the course of 4 h.

The release of ammonia, which appeared from the beginning of the running-in, was scrubbed on the scrubbing column. The reaction mixture was then maintained at 120° C. for 2 h in order to finish off the removal of the water.

The reaction medium was then gradually heated by bringing it: to 140° C. for 2 h, then to 160° C. for 2 h, then to 175° C. for 2 h, then to 185° C. for 2 h. It was cooled to 125° C. at the end of the reaction, and then the excess DETA was removed under reduced pressure. The product obtained after cooling to 60° C. and withdrawal from the reactor had a UDETA titer of 80-83% and contained 12-13% of TETU. This product therefore exhibited a purity much lower than 90%.

Comparative Example 2

Preparation of UDETA from DETA and Urea (R=1.1)

The same process as that described in example 1 was carried out, except that the DETA/urea molar ratio was 1.1:1 and the product obtained was not subjected to stripping under reduced pressure. The final product had a UDETA titer of 81% and contained 7% of DETA and 9.3% of TETU.

Comparative Example 3

Conventional Distillation of UDETA

The product resulting from comparative example 2 was subjected to a conventional distillation process.

The theoretical UDETA titer after removal of the residual DETA was 87%. After distillation at 170° C., under a pressure of 74 mbar, for 12 h, a final UDETA titer of only 64.5% was, however, obtained for this product, with an increase in the TETU content to 32.6%.

This example demonstrates that a distillation under vacuum under conventional conditions, at more than 150° C., does not make it possible to obtain UDETA having a purity of at least 90%, and, on the contrary, generates more impurities.

Comparative Example 4

Distillation of UDETA at More than 150° C.

UDETA was prepared according to a process identical to that of example 1, except that the distillation under reduced pressure was carried out at 180° C. The product obtained exhibited the following distribution by weight, as measured by NMR:
UDETA: 77.6%
DETA: 1.7%
TETU: 18%
Other impurities: 2.7%.

This example shows that an appropriate DETA/urea molar ratio (between 1.2 and 3.0) is not sufficient to obtain a product having the desired purity, and that it is also necessary to limit the distillation temperature to at most 150° C.

What is claimed is:
1. A method, wherein the method comprises:
a) producing a compound of formula (I):

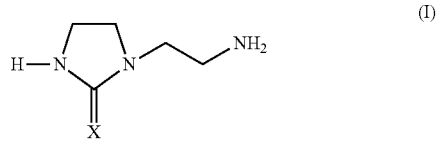

where X is oxygen or sulfur,
using a process comprising the successive steps of:
1) reacting, in a reaction medium, diethylenetriamine (DETA) with a urea compound chosen from urea and thiourea, in a DETA/urea compound molar ratio of between 1.2 and 3, at a temperature of at most 300° C.;
2) cooling the reaction medium;
3) removing the residual DETA by distillation in a column under reduced pressure at a temperature, at the bottom of the column, of at most 150° C.; and
b) producing a supramolecular material, a pharmaceutical compound, a phytosanitary product, or an additive for paints, paper or lubricants using the compound of formula (I) obtained in step a) as a synthesis synthon or reactant.

2. The method as claimed in claim 1, wherein the DETA/urea compound molar ratio is between 1.3 and 1.7.

3. The method as claimed in claim 1, wherein the distillation is carried out at a temperature, at the bottom of the column, of between 100 and 140° C.

4. The method as claimed in claim 1, wherein the distillation is carried out under a pressure of from 1 to 30 mbar.

5. The method as claimed in claim 1, wherein the distillation is a molecular distillation.

6. The method as claimed in claim 5, wherein the molecular distillation process comprises the following two successive steps:

1—a first distillation at a temperature of from 110° C. to 120° C., under a pressure of from 1 to 2 mbar, 2—a second distillation at a temperature between more than 120° C. and 135° C., under a pressure of from 0.01 to 0.02 mbar.

7. The method as claimed in claim 1, wherein the urea compound is introduced sequentially into the reaction medium.

8. The method as claimed in claim 1, wherein the urea compound is introduced into the heated reaction medium containing the DETA.

9. The method as claimed in claim 1, wherein the reaction is carried out at a temperature of between 100 and 250° C.

10. The method as claimed in claim 9, wherein the reaction medium is brought, during the reaction, from 110-140° C. to 150-190° C.

11. The method as claimed in claim 1, wherein the DETA removed is recycled into the process.

12. The method as claimed in claim 1, wherein the DETA/urea compound molar ratio is between 1.2 and 1.9.

13. The method as claimed in claim 1, wherein the DETA/urea compound molar ratio is between 1.3 and 1.6.

14. The method as claimed in claim 1, wherein the distillation is carried out at a temperature, at the bottom of the column, of between 120 and 130° C.

15. The method as claimed in claim 1, wherein the distillation is carried out under a pressure of from 1.5 to 10 mbar.

16. The method as claimed in claim 1, wherein the distillation is a short-path/wiped film distillation.

17. The method as claimed in claim 1, wherein the urea compound is introduced sequentially into the reaction medium in fractions of from 10 to 40% by weight relative to the total weight of urea compound processed.

18. The method as claimed in claim 1, wherein the reaction is carried out at a temperature of between 100 and 200° C.

\* \* \* \* \*